(12) United States Patent
Angres et al.

(10) Patent No.: US 11,268,942 B2
(45) Date of Patent: Mar. 8, 2022

(54) METHOD OF INSPECTING PACKAGES

(71) Applicant: Steinfurth Mess-Systeme GmbH, Essen (DE)

(72) Inventors: Johann Angres, Bochum (DE); Martin Falkenstein, Bochum (DE)

(73) Assignee: Steinfurth Mess-Systeme GmbH, Essen (DE)

( * ) Notice: Subject to any disclaimer, the term of this patent is extended or adjusted under 35 U.S.C. 154(b) by 81 days.

(21) Appl. No.: 16/633,430

(22) PCT Filed: Aug. 24, 2018

(86) PCT No.: PCT/EP2018/072935
§ 371 (c)(1),
(2) Date: Jan. 23, 2020

(87) PCT Pub. No.: WO2019/038444
PCT Pub. Date: Feb. 28, 2019

(65) Prior Publication Data
US 2020/0173973 A1    Jun. 4, 2020

(30) Foreign Application Priority Data
Aug. 24, 2017   (DE) .................. 10 2017 119 380.4

(51) Int. Cl.
*G01N 21/01*      (2006.01)
*G01N 33/14*      (2006.01)
(Continued)

(52) U.S. Cl.
CPC ............... *G01N 33/14* (2013.01); *G01J 5/52* (2013.01); *G01L 19/0092* (2013.01);
(Continued)

(58) Field of Classification Search
CPC .... G01N 21/359; G01N 21/84; G01N 33/025; G01N 33/03; G01N 2021/1706; G01J 3/108
(Continued)

(56) References Cited

U.S. PATENT DOCUMENTS 9,316,554 B1    4/2016  Eastman et al.
2007/0247620 A1*  10/2007  Koo ................. G01N 21/658
                                                    356/301

(Continued)

FOREIGN PATENT DOCUMENTS

DE    102013008003 A1   11/2014
EP        2348303 A1    7/2011
(Continued)

OTHER PUBLICATIONS

Office Action for European Application No. 18762478.8 dated Apr. 26, 2021, with its English summary, 10 pages.
(Continued)

*Primary Examiner* — Md M Rahman
(74) *Attorney, Agent, or Firm* — Rudy J. Ng; Bret E. Field; Bozicevic, Field & Francis LLP (57) ABSTRACT

The invention relates to a test device (10) for analysing, more particularly for detecting, non-destructively, pressure and temperature, and preferably for detecting a gas concentration in foodstuffs (50.4) contained in packaging (50), the test device having: —a detection assembly (30) for detecting at least one parameter in a foodstuff (50.4) contained in packaging (50), the parameter being specific to a property to be examined of the foodstuff (50.4). According to the invention, the test device (10) is designed as a hand-held device.

26 Claims, 1 Drawing Sheet

(51) Int. Cl.
  *G01J 5/52* (2022.01)
  *G01L 19/00* (2006.01)
  *G01N 1/22* (2006.01)
  *G01N 21/39* (2006.01)
(52) U.S. Cl.
  CPC ........... *G01N 1/2226* (2013.01); *G01N 21/39* (2013.01); *G01N 2021/399* (2013.01); *G01N 2201/0221* (2013.01)
(58) Field of Classification Search
  USPC ........................................................ 356/244
  See application file for complete search history.

(56) References Cited

U.S. PATENT DOCUMENTS

| | | | | |
|---|---|---|---|---|
| 2008/0117416 | A1* | 5/2008 | Hunter | G01N 21/65 356/301 |
| 2012/0204288 | A1* | 8/2012 | Allen | C12N 15/8273 800/278 |
| 2014/0007298 | A1* | 1/2014 | Allen | C12N 15/8261 800/290 |
| 2016/0011740 | A1* | 1/2016 | Schiefer | G06F 3/0488 345/173 |
| 2017/0028130 | A1* | 2/2017 | Perazzo | B65C 3/10 |

FOREIGN PATENT DOCUMENTS

| | | |
|---|---|---|
| RO | 128431 B1 | 5/2013 |
| WO | WO2010145892 A1 | 12/2010 |
| WO | WO2015036399 A1 | 3/2015 |
| WO | WO2015055743 A1 | 4/2015 |
| WO | WO2016001672 A1 | 1/2016 |
| WO | WO2019038444 A2 | 2/2019 |

OTHER PUBLICATIONS

Hossain et al., Optical fiber smartphone spectrometer, May 2016, Optics Letters 41(10):2237-2240, Abstract Only.
Search Report for Chliean Application No. 426-2020 dated Jun. 15, 2021, with its English translation, 18 pages.
Office Action for European Application No. 18762478.8 dated Aug. 17, 2021, with its English summary, 5 pages.

* cited by examiner

METHOD OF INSPECTING PACKAGES

The present invention relates to an inspection device of the type defined in more detail in the generic term of the independent device claim. Furthermore, the invention relates to a system under the generic term of independent system claim and a method under the generic term of independent procedural claim.

From the state of the art, various methods are known for the inspection of food in packaging. Such methods concern, for example, all forms of beverages and dairy products, in the form of cheese, yoghurt, meat products, sweets, spices and the like. Well known are for example shelf life inspections. Food manufacturers indicate the date of minimum retention (Best before for short) for their food, up to which date the food can be consumed without any significant loss of taste and quality or health risk, provided it is stored properly (in particular compliance with the storage temperature specified in connection with the minimum retention date). The best before date is not an expiration date, as the food is generally still fit for consumption after the stated best before date.

Food manufacturers shall keep samples of each production batch of food to enable them to demonstrate the quality of the batch of food products. In addition, the individual samples of food from a series are checked for quality at specified times. However, the samples of food already examined are usually unusable after the inspection, as the packaging has been opened and air could therefore get into the food. In addition, the storage temperature is usually also changed by the inspection, which is also undesirable and can have a negative effect on the food. For this reason, the food manufacturer must keep a sufficient number of samples of food to be able to perform destructive sample measurements at the relevant times. As a result, the food manufacturer has to keep a corresponding number of samples from a series of foods in stock for later inspection. Consequently, the need for storage and stockpiling and the resulting losses in food production are very high.

Furthermore, state of the art inspection of food in packaging is very costly and inflexible. Usually, such inspections comprise several steps to be performed in the laboratory, during which the sample has to be prepared extensively and analyzed by means of complex stationary devices. One aim of such inspection is, for example, the determination of the $CO_2$ content of carbonated liquid foods.

In the case of such food in the form of beverages, it has been determined that the pressure present in the bottle and the material of the bottle, for example glass, porcelain or PET, is decisive for the quality and taste of the beverages. This means that the detecting of pressure by means of appropriate inspections is also of particular importance. Again, the benefit of these studies is often limited by the flexibility and (cost) effort involved.

The object of the present invention is thus to overcome, at least partially, the disadvantages of the prior art described above. In particular, it is the object of the present invention to provide an improved possibility for the inspection of food. In particular, the packaging of the food should remain unimpaired or fully functional during the inspection in order to ensure the best possible shelf life of the food.

The preceding object is solved by an inspection device with the characteristics of the independent device claim, a system with the characteristics of the independent system claim and a method with the characteristics of the independent method claim. Further features and details of the invention result from the respective dependent claims, the description and the drawings. In this context, features and details described in connection with the inspection device according to the invention are of course also valid in connection with the inventive system as well as the inventive method, and vice versa, so that with regard to disclosure, the individual aspects of the invention are or can always be mutually referred to.

The object is solved in particular by an inspection device for inspecting, especially for non-destructive pressure and temperature measurement, preferably for $CO_2$ detection, for food in packaging, comprising
a detection arrangement for detecting at least one parameter in a food in a package, the parameter being specific to a characteristic of the food to be investigated.

In particular, it is intended that the inspection device is configured as a handheld device. This enables particularly flexible and cost-effective detecting, especially when mobile, without the use of stationary detecting devices. In this connection, the detection of at least one parameter may be performed as a detection, in particular a measurement, of pressure and/or temperature in the food in order to determine a $CO_2$ content in the food and/or in the packaging. In other words, the parameters pressure and/or temperature are specific to the $CO_2$ content, i.e. the $CO_2$ content can be determined (at least approximately) on the basis of these parameters. Furthermore, as an alternative or in addition to the $CO_2$ content, other properties of the food to be inspected may also be of interest. These can be physical properties or quality properties of the food. For example, the parameter detected may also directly form the characteristic to be inspected (this is the case, for example, when the pressure or temperature of the food is inspected as a corresponding parameter). Nevertheless, several parameters can be detected within the scope of the invention in order to determine a (single) characteristic of the food (e.g. pressure and temperature can be compared and/or evaluated in combination to obtain a $CO_2$ content.). A particular advantage results from the fact that the inspection device according to the invention is completely configured as a handheld device. This means that such an inspection—usually performed by stationary equipment—can now be performed easily and cost-effectively.

Advantageously, a handheld (handheld device) is understood to be a portable electronic device in which a mobile energy supply is preferably provided, e.g. by at least one (possibly attached or replaceable) rechargeable battery and/or at least one (possibly attached or replaceable) non-rechargeable battery. The handheld may be configured as a handheld device to be held in one hand only during use, so that the handheld device can be made portable and/or operable by one hand.

The terms "food" and "packaging" are mentioned below, meaning in particular that they are the same or similar food. These foods may also be arranged in the same or similar packaging. The term "sample" refers to the food to be analyzed in the packaging, and "product" refers to the combination of food and packaging.

The characteristic to be inspected, in particular the $CO_2$ content of a food, can be determined, for example, by means of a specification such as a calculation formula or a law. This is how the Henry Dalton law describes the solubility of gases in a liquid. Accordingly, parameters such as the partial pressure (or even approximately the total pressure) of the gas as well as the concentration of the gas in the solvent (e.g. a liquid of the food) can be used to determine the characteristic to be inspected. It is also conceivable that boundary conditions must be defined to determine the characteristic to be inspected. For this purpose, further parameters can be detected, such as a temperature of the food.

It may also be provided that the characteristic to be inspected is a $CO_2$ content of the food in the packaging. This allows a reliable assessment of the quality of the food. In particular, the $CO_2$ content can be used to check the shelf life of the food. The portable configuration of the inspection device as a handheld is of great advantage here, as the inspection can then be performed not only in the laboratory, but also directly at the point of sale or by the customer.

Furthermore, the invention may provide that the parameter is a pressure and/or a temperature at the food. The pressure can be, for example, a total pressure and/or a partial pressure of the food in the packaging, in order to reliably determine the characteristic to be inspected on the basis of the temperature. For example, the temperature of the food is measured separately from the pressure, i.e. by separate sensors, although the sensors can also measure the temperature simultaneously.

Different pressures and/or different physical properties can also be detected as parameters, and/or from one of the detected parameters (e.g. from the total pressure) the other parameter (such as the partial pressure) can be calculated. For example, only the total pressure of the food in the packaging can be detected in a simple way, but the partial pressure may be necessary to determine the characteristic to be inspected (in particular according to Henry Dalton's law for determining the $CO_2$ content). Thus, to solve this problem, further information may be necessary, i.e. at least one calibration information, to determine the partial pressure from the total pressure and/or to determine the characteristic to be inspected only on the basis of the parameter detected.

It is therefore advantageous in the context of the invention, if at least one calibration information is used for the performance of the detection and/or for the determination of the characteristic to be examined, in particular is selected. Preferably, the selection is made from several pre-stored calibration information, e.g. from a database. The calibration information can be used to indicate how the result (e.g. $CO_2$ content) and/or the other parameter (e.g. partial pressure) is calculated from the measured parameter (e.g. total pressure) for a specific food and/or packaging. For this purpose, for example, a mathematical formula and/or an algorithm can be parameterized by the calibration information.

To select the correct calibration information, additional information, e.g. about the type of food and/or packaging, may need to be known. Such additional information for the selection of the calibration information can be e.g. information about the food in the package and/or about the package (product specific information), e.g. an image information (like a photo of the food in the package), a manual selection of the food and/or the package, information about a geometry of the package, a metrological registration of the package or the like. This additional information can, for example, be acquired in a separate step by an external device. The additional information can then be used to select the at least one calibration information, which then serves to determine the characteristic and/or the other parameter from the acquired parameter.

Optionally, it may be provided that the detection arrangement has at least one transmitter unit for transmitting a measuring effect and/or at least one receiver unit for detecting the measuring effect transmitted. Preferably, the transmitting unit may be configured as a radiation source, in particular a laser source, and/or the receiving unit may be configured as an optical sensor and/or the measuring effect may be a radiation, in particular laser radiation. The detection arrangement is configured, for example, to detect a change in a spectrum of radiation or laser radiation that is specific to the parameter to be detected. For example, the optical sensor has at least one photodiode, so that a spectrum can be determined if the wavelength of the radiation or laser radiation changes during detection. This enables the detecting to be performed simply and cost-effectively. Furthermore, when using a compact laser, such as a diode laser, as a radiation source, the detection can also be performed in a particularly flexible and mobile manner. The advantage of this is that the parameter to be detected can be reliably determined by a detecting result such as the spectrum. This can be done, for example, by evaluating peaks or the like in the spectrum, whereby a width (e.g. half-value width) of these peaks may be specific to the parameter.

It is conceivable that the receiving unit of the detection arrangement is configured as at least one sensor comprising at least one photodiode or the like. The at least one transmitter unit is configured, for example, as a light source (radiation source), which preferably has a semiconductor laser, in particular a tunable semiconductor laser. This may, for example, have at least one laser diode to emit the radiation. For example, the light source is operated with an electric current of variable intensity. The light source may be configured to be tuned according to the current intensity. The wavelength of the radiation emitted by the light source is thus dependent on the current and, if necessary, the temperature, whereby the average (center) wavelength can be in the range of 500 to 4000 nm, preferably 1500 to 2500 nm. This allows an appropriately broad spectrum to be reliably detected by the detection arrangement. For cooling, the laser diode of the light source can be mounted on a cooling element, e.g. a Peltier element.

Optionally, the inspection device and/or the detection arrangement may also have at least one means for detecting a density and/or an oxygen content (in each case, e.g. of the food) and/or a torque during packaging, in particular a closure of the packaging. This detecting can be combined with the detecting of the pressure and/or the $CO_2$ content to increase the reliability of the inspection.

A further advantage within the scope of the invention is achievable if a positioning structure is provided to perform an external positioning (i.e. positioning from the outside) of the detection arrangement on the packaging, in particular according to a predetermined arrangement, in particular with predetermined distances and/or centered to the packaging. The background to this is that an exact positioning with specified distances and angles to the packaging geometry may be necessary in order to perform the detection correctly. In particular, at least one calibration information (possibly including information on the geometry of the packaging) is used in the detecting to reliably determine the at least one parameter and/or the characteristic of the food. Since this calibration information may depend on the exact geometric alignment, this must be guaranteed by the positioning structure. For this purpose, for example, the sensors, such as a transmitter unit and/or receiver unit and/or a temperature sensor, are attached to the inspection device via a housing and/or a frame in a set and defined manner.

In a further possibility, it may be provided that a positioning structure is provided for at least partial arrangement of the package with the food in an arrangement area as a measuring area, wherein a transmitting unit and a receiving unit of the detection arrangement are aligned with the measuring area by the positioning structure. For example, the sensors (e.g. the receiver unit and transmitter unit form one sensor) of the detection assembly may be attached to the positioning structure to allow positioning and/or placement and/or alignment of the sensors on the packaging or the arrangement area. In addition, the positioning structure may include a retaining unit to allow alignment and/or detachable attachment of the packaging to the positioning structure. It is advantageous if the measuring range comprises the measuring distance, i.e. the distance that a measuring effect, in particular a laser beam, passes through the food.

The positioning structure mentioned above can also be used to ensure that different measurements can be taken in different (predefined) positions. From the respective measurement results in the corresponding positions, further measured values (detection of additional information) can then be generated or disturbing influences can be compensated in order to improve the accuracy of the food characteristic to be inspected or the inspection result.

Furthermore, it is advantageous if a communication device is provided in the inspection device in order to perform data communication, in particular wireless data communication, with a mobile communication device and/or a central data processing system in order to transmit a result of the detection via data communication. The result of the detection (detection result) can be, for example, a measured value of at least one parameter or the like. In particular, a transfer is then necessary in order to evaluate the detecting result separately from the inspection device and to determine an inspection result. Alternatively or additionally, the inspection by e.g. an inspection unit can also be performed by the inspection device itself, so that the inspection device provides the inspection result. This enables additional devices to be dispensed with in order to reduce the technical effort. However, for some applications it is advantageous if the inspection is performed by an external device, as this allows more complex calculations and/or a central provision of calibration information (e.g. by a database). The communication (especially wireless or wired) takes place, for example, between at least two of the following devices:
- the communication device of the inspection device,
- a mobile communication device, in particular mobile radio equipment, e.g. a mobile telephone and/or smartphone,
- a data processing system, e.g. at least one server of a so-called "cloud".

Communication can also be advantageously performed as a visual data transmission, e.g. by means of a QR code. In this case, the communication device may have, for example, a display to show a QR code. It is also conceivable that the communication device may have a QR Code scanner or the like to receive data.

The data processing unit is configured, for example, as at least one computer and also comprises, for example, at least one data memory, so that at least one database can be provided by the data processing unit. Due to the data processing unit and/or the mobile communication device, i.e. the external devices, more extensive and complex inspections are possible than can be done with the inspection device. This means that the inspection device according to the invention can do without complex inspection electronics, thus improving the mobility of the inspection device and reducing costs.

It is also advantageous if a retaining unit, preferably a positioning unit, is provided to attach the inspection device to the packaging. The retaining unit, in particular positioning unit, can, for example, have a conical receptacle or the like to enable a form-fit connection to the packaging, in particular to a head area and/or closure of the packaging. For example, the packaging is configured as a bottle, in particular as a PET (polyethylene terephthalate) bottle or as a glass bottle or the like, and accordingly has at least partially a transparent wall (i.e. a transparent area). In order to be able to perform a measurement on the food in the packaging, it is necessary to position the sensors of the detection arrangement in such a way that they are aligned with this transparent area. The retaining unit can be used for this purpose, as it enables a predefined and thus known arrangement and orientation of the packaging.

Preferably, the invention may provide for a retaining unit. This can, for example, be configured as a closing gripper (especially a so-called "chuck") for torque measurement. The inspection device and/or the retaining unit may also have at least one means of detecting an oxygen content and/or a content of other gases and/or an alcohol content. In particular, the retaining unit is configured to be attached to a bottle closure of the packaging configured as a bottle, the retaining unit preferably having a rotating and/or pivoting mechanism. In particular, the retaining unit or the chuck serves as a means of attaching, so that the inspection device according to the invention can be reliably and securely attached to the packaging. The inspection device can be attached to the packaging (container) with the retaining unit as centering unit, if necessary, to a so-called "PET neck ring" or similar. Preferably, a defined set attachment to the container in the area of the gas space (head space) of the packaging can also be used for attaching the retaining unit. It is also advantageous if the retaining unit is used to detect a torque when opening the packaging, as this allows conclusions to be drawn about the characteristic to be inspected, in particular a $CO_2$ content. For this purpose, for example, a lid (as a closure) of the packaging can be opened slowly, e.g. manually. Due to the attachment of the retaining unit to the closure or lid, a force is thus exerted on the retaining unit, in particular as a torsional force, which can be detected and/or measured by a torque measuring system at the retaining unit. The measured values determined here can then be automatically evaluated to determine an inspection result and/or to determine the characteristic to be examined. In particular, the (product-destroying) torque detection by the torque measuring system can be performed additionally and secondarily to the (non-destructive) optical detection of the parameter by means of the transmitting and receiving unit and/or the temperature sensor, e.g. in order to confirm this critical result in case of a critical inspection result of the optical detection.

It may also be possible that a retaining unit is configured to adapt to a head space of a package configured as a bottle, preferably to attach the inspection device concentrically to a bottle closure. In other words, the bottle closure in the headspace can form a closure or closure for the bottle, which has regularly predefined and thus known geometries. Thus, the retaining unit can be adapted to this geometry from the outset and/or, if necessary, be configured to be adaptable to different geometries, e.g. by means of an adjustment mechanism.

Furthermore, it is advantageous if a retaining unit is provided within the scope of the invention and is configured as a centering unit so that a centering of the inspection device on the packaging in a measuring position is effected by the retaining unit. The measuring position is used to detect at least one parameter, and therefore offers a positioning of the packaging that is required for detecting. This enables reliable detection, especially as a measurement.

It is also advantageous if the transmitting unit is aligned with the receiving unit and an arrangement area in such a way that a measuring effect first reaches the arrangement area and then the receiving unit in order to detect a change in the measuring effect caused by the food. For example, the measuring effect is an electromagnetic radiation such as laser radiation, which reaches the food through a wall of the packaging and is changed by the molecules of the food (e.g. by absorption). This change can be wavelength-dependent, and broadening mechanisms can be used if necessary, so that the change can be evaluated using an absorption spectrum. For example, the absorption spectrum is detected by the receiving unit by automatically changing the wavelength of the emitted radiation or laser radiation during the detection.

Furthermore, in the case of the inspection device in accordance with the invention, it is possible that at least one light source, in particular in the form of a tunable diode laser, is provided in the detection arrangement, and a measuring effect as emitted light of the light source can be detected by an optical sensor in order to perform a $CO_2$ content measurement the food. In doing so, a wavelength of the emitted light can be changed to operate the tunable light source. In particular, the light source can be configured as an infrared laser and the sensor as an infrared sensor. Thus, a varying wavelength in the infrared range can be emitted and detected.

Furthermore, it is conceivable within the scope of the invention that a display device is provided for the representation of a maximum three-stage or maximum four-stage inspection result. The display device is used in particular for displaying an inspection result, preferably a display of the measurement results. Alternatively or additionally, the display can be made on a display medium of a mobile communication device. The display device and/or the display means is configured, for example, as an electronic display and/or touch screen and/or the like.

It may also be possible that an energy storage device, preferably an accumulator, is provided for portable operation of the inspection device for mobile energy supply. The energy storage device can be so compact that it can be arranged in a housing of the inspection device. This enables the training as a handheld in a simple way.

It is also conceivable that the detection arrangement may optionally include an optical temperature sensor, in particular a bolometer or pyrometer, to detect a temperature at the food in the packaging. This also means that a temperature is detected on a surface of the packaging. It may be possible for the temperature sensor to be directed towards an area of the package below a gaseous phase of the food and/or below a level of the food in the package to detect the temperature and accordingly detect the temperature in that area of the food in the liquid. The temperature sensor can have a light source, preferably a laser source, and/or an optical sensor for detection.

The invention also relates to a system for inspection, in particular for non-destructive pressure and temperature detection, preferably for $CO_2$ detection, of food in packaging, comprising:
a inspection device, in particular according to the invention, for detecting at least one parameter in a food in a package, the parameter being specific to a characteristic of the food to be inspected,
an inspection unit for evaluating the detection and in particular at least one further piece of information, such as calibration information, in order to determine the characteristic of the food to be inspected, wherein preferably the inspection device is configured as a hand-held device.

Thus, the system according to the invention brings the same advantages as they have been described in detail with respect to an inspection device according to the invention. In addition, the system may have an inspection device that is in accordance with the invention.

Preferably, the inspection device is configured to be placed on the outside of the packaging in order to perform the detection in a non-destructive manner. In other words, the packaging can remain sealed, and thus the detection of parameters of the food can take place indirectly through the packaging.

For example, in the system according to the invention, the inspection unit can be configured as an electronic processor, which is optionally connected to a data memory in order to perform the inspection as a data processing. Furthermore, by means of the detection, i.e. at least one result of the detection or measured value, by the inspection and, if necessary, by means of at least one calibration information, information about the characteristic to be inspected can be determined as the result of the inspection. This enables, for example, the examination of the quality of food simply, cost-effectively and flexibly.

Preferably, the inspection unit may be part of the inspection device, so that the inspection is performed by the inspection device. This makes the inspection compact and cost-effective without the need for additional tools.

It may be advantageous if the invention provides for a mobile communication device which includes the inspection unit in order to perform the inspection separately from the inspection device. For example, the communication device is configured as a smartphone and therefore has a powerful processor for inspection. It may also be possible that the inspection for determining an inspection result is only partially performed by the inspection unit and, if necessary, another inspection unit (e.g. a data processing system, such as a server) is used. For this purpose, a networked inspection can be provided, which uses a communication e.g. with a cloud.

It is also advantageous if a mobile communication device is provided, which has at least one sensor element in order to detect information about the foods in the packaging and/or about the packaging (in particular product-specific information) separately from the inspection device, so that the inspection, in particular the determination of the characteristic of the food to be examined, is performed as a function of the detected information and the detected parameter. For example, the sensor element of the communication device is configured as an image sensor to detect image information (photo) of the food in the packaging. By analyzing this image information, e.g. by the communication device itself or by a data processing system, at least one further piece of information about the food in the packaging and/or about the packaging (in particular product-specific information) can then be determined. Such information is, for example, information on the type of food and/or information on the packaging (geometry, printing or the like). In other words, the information collected by the communication device can be used to classify the product under inspection. Alternatively or additionally (e.g. in case of failed classification), a manual selection of the information, e.g. from a list, can also be made at the communication device, if necessary. This information can then be used to perform the detection and/or inspection, e.g. to select at least one calibration information.

It may also be possible that the inspection device has a display means for displaying a code, preferably bar codes and/or QR codes, and/or an image sensor, such as a scanner, for scanning such a code. The display means and/or the image sensor may, for example, be part of a communication device of the inspection device to effect data exchange, e.g.

to exchange data with a communication device or the like. The communication device is, for example, a smartphone or a camera or the like, which can be used to select and/or detect at information about the food in the packaging and/or about the packaging. The communication device can also be used to initiate the inspection based on the parameters detected and/or to perform and/or initiate an inspection of the detecting. For this purpose, the detected parameters (e.g. the measured values) can be transmitted, e.g. from the inspection device to the communication device or also to another device for inspection by means of data exchange. In other words, the display means may be configured to show a result of the detection of the parameters (especially coded). This result may, for example, be at least one reading of a temperature and/or pressure sensed in the food.

Also, the subject of the invention is a method of inspection, in particular for the non-destructive measurement of pressure and temperature, preferably for $CO_2$ detection, of food in packaging.

In particular, it is intended that the following steps are performed, preferably one after the other or in any order, whereby individual steps can also be performed repeatedly if necessary:
(a) mobile or stationary detection of at least one parameter in a food in a package by a portable inspection device, the parameter being specific to a characteristic of the food to be inspected
(b) evaluating at least the detecting of at least one parameter to determine an inspection result,
(c) output of the inspection result.

Thus, the inventive method brings about the same advantages as those described in detail with respect to an inventive inspection device and/or an inventive system. In addition, the method according to the invention can be used to operate a system according to the invention and/or an inspection device according to the invention.

The determination of the inspection result and in particular of a $CO_2$ content of the food can be advantageously performed by means of at least one measured value of the detecting, e.g. by the inspection device or by an external device.

Advantageously, one (theoretical, mathematical, chemical and/or physical) model or several (theoretical, mathematical, chemical and/or physical) models and/or a parameterization of the at least one model dependent on the detection can be used for the inspection and/or determination of the $CO_2$ content. The selection of the model and/or the parameterization may depend on the geometry of the packaging and/or on a diameter of a bottleneck of the packaging and, if necessary, on the food itself.

Preferably, a geometry of the packaging, especially of a bottle, can be used to select in particular one of several (e.g. at least 5 or at least 10) models for inspection. For this purpose, for example, an input can be made via an input device such as a touch screen of the inspection device. For this selection, a data exchange can also be performed, e.g. by means of a QR code.

The detection or several detections of the at least one parameter in an inspection device according to the invention and/or in a method according to the invention, in particular the detection and/or repeated detections according to step a), can be performed in particular by the means of detection at a static position on the packaging (preferably on a bottle neck e.g. by one or more sensors) or alternatively at several positions on the packaging (e.g. by the same sensor by means of a movement of the sensor, the inspection device or the packaging). In other words, it is also possible that several entries are made at different (possibly predefined) positions, either consecutively or simultaneously. For example, when using multiple positions where the detection is performed, the inspection device (e.g. due to the positioning structure) and the packaging can be moved relative to each other while the detection is being performed. In this way, additional information can be determined on the basis of the detecting, which is specific to a geometry of the packaging, for example. In particular, the geometry of the packaging can be determined on the basis of the capture if the positions of the captures are taken into account in the inspection. For example, a result (measured value) of the detection and/or the determined spectrum depends on the geometry. For simplified relative movement between the measuring device and the packaging, the latter is configured, for example, as a fork-shaped inspection instrument or the like. The inspection device may have a recess for receiving and/or displacing and/or moving the package (in particular the neck of the bottle) for several positions within the recess. The determined geometry can, for example, be taken into account in the inspection.

In particular, the method according to the invention involves the detection of a total pressure in a head space of the packaging and/or the detection of a partial pressure of a gas (e.g. $CO_2$) of the gas phase in the packaging. For example, the $CO_2$ content dissolved in the liquid can be determined for inspection and determination of the characteristic of the food according to the physical law of Henry & Dalton. For this purpose, for example, at least one arithmetic calculation can be performed by the inspection unit and/or by the mobile communication device and/or by the data processing system. Preferably, the pressure is measured using a spectrum, preferably an absorption spectrum, of a measuring effect, in particular electromagnetic waves (e.g. light or laser beam). This can include an inspection of a line spread, whereby this depends, among other things, on an absolute pressure of the inspection object. The higher the gas pressure, the flatter and wider the absorption curves become. The shape of the absorption curve can be used to draw conclusions about the total pressure. In other words, the total pressure can be detected and/or evaluated in accordance with the method according to the invention by means of a curve inspection in the spectrum. Which parameters are used for the inspection depends, for example, on at least one calibration information (i.e. the calibration data).

Furthermore, it may be possible that an optical (in particular non-destructive) determination of a pressure and/or a temperature is performed on the food. Alternatively or in addition, the inspection in accordance with the method specified in the invention may provide a transparency inspection for the packaging and/or a geometry measurement and/or a position determination on the packaging and/or a torque measurement. It may also be possible, for example, to perform a dynamic transparency check of the measuring section (e.g. to detect foam and/or stickers) using the inspection device according to the invention.

Furthermore, it may be provided within the scope of the method according to the invention that the inspection result is formed in a maximum of three steps, preferably according to a traffic light gradation, whereby preferably for this purpose an intermediate result of the inspection is compared with at least two different threshold values, so that a three-step classification is made on the basis of the comparison. For example, this classification can be made on the basis of the at least one calibration information, so that the classification is performed depending on the food in the packaging. This is because different limit values can be used to determine the quality of different foods. In particular, therefore, the at least one calibration information includes the at least one threshold value for classification. It is also conceivable that warning limits for product quality are inspected and/or output. The output according to step c) can be made, for example, on an external device, such as a PC or tablet or telephone, or directly on the inspection device.

Optionally, in the method according to the invention, it may be provided that prior to step a) information, preferably image information, is detected by an optical sensor element, preferably of a mobile communication device, in particular a mobile radio communication device, about the packaging and/or the food in the packaging, and in step b) the inspection is also performed on the basis of this information, preferably in order to take into account the type of packaging and/or the food. It is advantageous if the sensor element (e.g. as an optical unit) is used to detect the packaging and/or the product (the sample). Thus, information about the product, such as a barcode or other identification feature, such as a photograph or manual product selection, can be determined to determine the type of food and taken into account in the inspection.

A further advantage within the scope of the invention is achievable if, prior to step a), at least information about the packaging and/or about the food is transmitted to an external data processing system by a communication of the inspection device or a mobile communication device, and at least one piece of calibration information is determined on the basis of a database of the data processing system as a function of the transmitted information in order to perform the detection according to step a) and/or the inspection according to step b) on the basis of the calibration information. For example, tuning and/or calibration can be performed during spectroscopic measurement using the calibration information. Preferably, calibration data are stored in the database as product specific information and/or characterization parameters to provide at least one calibration information. The calibration data include e.g. calibration curves, which are created for different samples and/or products (food in packaging).

The inspection device therefore only records raw data, for example, and the inspection based on the calibration information can then be performed separately from the inspection device, e.g. by an external device.

Furthermore, it may be advantageous according to the invention that step a) and/or b) and/or c) is performed autonomously by the inspection device. Autonomous execution means that external devices do not have to be used for the corresponding steps. This has the advantage that a quick and simplified implementation is possible.

Furthermore, it may be provided within the scope of the invention that steps b) and/or c) are at least partially performed by an external device, preferably by the data processing system and/or by the mobile communication device, whereby preferably for this purpose a data communication of the inspection device is performed via a data network with the external device. This also allows for complex processing, for which, for example, a stationary computer is required. At least the detection can be performed by the portable inspection device, e.g. as a handheld. This significantly improves the flexibility of the method.

According to a further possibility, the method according to the invention may provide that the detection according to step a) and/or the inspection according to step b) comprises a spectroscopic inspection of a light beam. In particular, the parameters can be determined particularly reliably in the spectrum.

It is also conceivable that prior to step b) at least one geometric characteristic of the packaging is detected, preferably by a mobile communication device, preferably by image detecting, and inspected in step b). This allows further information to be used, such as the geometric characteristic, to select, for example, at least one calibration information depending on this information and/or a classification based on this information.

In addition, it is advantageous to determine information about the packaging and, preferably at step b) of a method according to the invention, to combine and/or compare and/or jointly inspect this information with a result of the detection in order to determine a pressure in a head space of the packaging. Preferably, a calculation of a $CO_2$ content is performed on the basis of a result of the inspection according to step b), whereby the result of this calculation can be presented as an inspection result according to step c). In particular, the information about the packaging (e.g. as image information) is detected by a mobile communication device and is used to determine the properties of the packaging, e.g. type, material, geometry or bottleneck dimensions. This information and/or the specific characteristics can then be used with the result of the detection according to step a), i.e. in particular the laser data, to calculate the pressure in the headspace of the packaging, in particular a partial pressure and/or a total pressure.

Furthermore, it may be advantageous in the context of the invention that, according to step a), at least the temperature and/or pressure is measured in order to determine a gas concentration in the package from the measured values of this measurement, preferably in dependence on at least one calibration information determined in dependence on the food in the package (and/or the packaging). For example, the at least one calibration information is automatically selected depending on a classification, and if necessary, alternatively or additionally selected manually. The classification is performed, for example, to determine a type of food and/or packaging, and can be performed, if necessary, on the basis of product-specific information which is detected by at least one sensor element. The sensor element is, for example, integrated in the inspection device or in the communication device and preferably performs a metrological detecting and/or an image detecting of the food in the packaging, preferably non-destructively (i.e. without damage and/or without opening the packaging).

It is further possible within the scope of the invention that reference measurements are repeatedly performed on samples in order to determine at least one calibration information (calibration data). In particular, at least one measurement result of the respective sample measurement is permanently stored and, if necessary, provided by a database. It is recommended that a separate reference measurement is made for each food product (i.e. the same food, e.g. non-alcoholic beer of a certain brand) in order to obtain exact reference measurements for a later comparison measurement. Comparison measurement is understood to mean, for example, the detection of at least one parameter, whereby a result of the detection is compared with the reference measurement during inspection in order to determine the characteristic.

The present method can be performed for different food in different packaging. Different calibration information can be determined for different foods and/or packaging and stored in the database. It may also be possible that an identifier is determined and provided for each of the different food or packaging. During an inspection, information about the food and/or packaging may be acquired by a device, such as a mobile communication device, prior to being acquired by the inspection device of the invention. The identifier is then compared with information about the food or packaging, such as image information, to determine the food and/or packaging under investigation. Depending on this determination, the detection and/or inspection can then be performed, in which at least one calibration information selected depending on the comparison is used.

According to the invention, it may be provided that for the determination of at least one calibration information a direct sample measurement of the food is performed by destroying the packaging. It is conceivable here that the packaging is punctured, e.g. by a piercing agent, so that at least one measuring sensor can be inserted into the packaging. With this measuring sensor it is then possible to measure at least one physical, chemical and/or biological characteristic of the food. These can be, for example, the temperature, pressure, moisture, electrical resistance or other properties of the food that can be directly measured. The direct sample measurement thus has the advantage that the measurement results from the measuring sensor take place under exclusion of the measuring environment and thus without measuring errors. This allows an exact sample measurement to take place with a high accuracy of the measured characteristic of the food. However, direct sample measurement also has the disadvantage that the packaging cannot usually be resealed, so that at the end of the sample measurement the food with the packaging is unusable, especially for later measurements. This is due on the one hand to the fact that air penetrates the packaging after the measurement and on the other hand to the fact that e.g. an overpressure or an inert gas can escape after the direct sample measurement. Furthermore, the cold chain of the measured food sample is usually interrupted by the measurement. The at least one calibration information thus determined can then be used for a large number of further inspections by the inspection instrument, and thus enable non-destructive inspection.

Furthermore, it is conceivable within the scope of the invention that during the inspection by the inspection device according to the invention, an indirect sample measurement of the food takes place during which a non-destructive inspection is performed. In this case, the packaging generally remains intact, since the sample measurements are performed exclusively through the sealed packaging. In particular, physical, chemical and/or biological properties of the food can be measured preferably without contact (with the food) through the packaging. This can be done e.g. by optical, inductive, capacitive and/or electromagnetic detection, especially measurements, preferably by the detection arrangement. X-ray or ultrasound measurements as well as magnetic resonance measurements or the like can also be used.

The method according to the invention may also provide that the inspection shall include at least the measurement of the temperature or pressure inside the packaging. By means of the above-mentioned and measured properties and, if necessary, the other physical, chemical and/or biological properties of the food, it is then possible to draw conclusions about the quality and taste of the food and/or the best-before date as the result of the inspection.

Furthermore, it is conceivable within the scope of the invention that a gas content in the packaging may be determined on the basis of detection, in particular from measured values of temperature and pressure. In particular, a calculation function may be used for this purpose which requires as input values at least the temperature and pressure in a package and then uses these input values to determine the gas content in the corresponding food. An inspection unit can be used for this purpose. Preferably, for each food (e.g. beer, lemonade, etc.) a corresponding calculation function is determined as a function of temperature and pressure, with the aid of which the corresponding gas content in the packaging can then be determined. Especially with beverages that are arranged in liquid containers or bottles, the gas content (e.g. $CO_2$) plays a significant role. It is also advantageous if at least one calibration information has or indicates the corresponding calculation function.

Within the scope of the invention it is optionally provided that e.g. the gas content at least in the packaging or in the food has a substantial influence on the shelf life. This means that the gas content (e.g. $CO_2$ for beer) also has a significant influence on the best-before date. If the gas content in the packaging is reduced over the course of time, e.g. because a part diffuses through the packaging, the shelf life of the food also decreases accordingly over time. This means that it is preferably necessary to check the gas content in the packaging and/or in the food regularly at intervals, for example at predefined intervals $\Delta t$.

The above-mentioned food can be a drink in particular, by which liquid food is meant. It is conceivable that the beverage may contain $CO_2$ in particular, which—as already described—has a significant effect on the quality and taste of the beverage. Thus, the $CO_2$ content also provides a clear conclusion on the quality and taste of the beverage and the best before date to be achieved.

In the method according to the invention, it may optionally be provided that in a step prior to a detection of the at least one parameter by the inspection device, the package with the food is at least shaken or brought to a predefined temperature in order to achieve a state of equilibrium within the package. The state of equilibrium within the package is important for accurate sample measurement, both for indirect and direct measurement. Otherwise, measurement errors may occur under certain circumstances. Particularly in the case of beverages containing $CO_2$, shaking creates a uniform partial pressure in the gas space and the liquid space of the packaging. It is also possible to bring the packaging with the food to a predefined temperature prior to the inspection device detects it, in order to directly exclude temperature-related measuring errors. It is recommended that a homogeneous temperature is also present inside the packaging.

Furthermore, according to the invention, it may be provided that in a step prior to an detection by the inspection device according to the invention, at least one geometric characteristic of the packaging is acquired, e.g. metrologically, e.g. by the inspection device or a device external to it, such as a mobile communication device. The geometric characteristic mentioned may, for example, be the external dimensions of the packaging, particularly in the measuring area, for example the neck of the bottle or the head space. For example, the outer diameter of a beverage bottle neck can be measured. The wall thickness of the packaging in the measuring range can also be measured technically, so that an exact measurement can be made within the packaging. Here, for example, the inner diameter of a bottle neck can be determined in the measuring range, which can be used to determine the running length of the light beam, for example. But the refractive index of the packaging material of the packaging can also be measured, for example. To record this geometric characteristic, image information can be detected and inspected, for example. Overall, the detecting of the geometrical characteristics of the packaging serves to enable indirect sample measurement or to exclude measurement errors due to geometrical packaging tolerances.

The invention also allows the detection of at least one parameter of the food by at least one optical measurement through the packaging. This optical measurement does not have to take place in the visible light range for humans. For example, a measurement can also take place in the infrared or ultraviolet radiation range. Other electromagnetic spectra of light are also conceivable. As mentioned previously, a measurement can also be made by ultrasound or X-rays.

Furthermore, it is conceivable within the scope of the method according to the invention that the packaging is at least partially (light-)transparent or at least has an optically transparent measuring window. This optically transparent area does not have to be transparent to the human eye, but must only be penetrable for the optical measurements described above in order to be able to measure the properties of the food in the packaging in an optical manner without measurement errors. It goes without saying that a corresponding optical sensor measures geometrically in the optically transparent area of the packaging. For this purpose, an appropriate light source emitting the optical radiation can be arranged on an opposite side of the optical sensor. Of course, several optical sensors as well as light sources for performing the method according to the invention are also conceivable, which do not all have to function in the same frequency spectrum or the same wavelength. On the contrary, light sources that at least temporarily emit different light of different wavelengths can facilitate optical measurement. Also monochromatic, polarized and/or pulsed light etc. can be used for optical measurement.

With the method according to the invention, it is also conceivable that the packaging takes up and encloses the food in a pressure-tight manner. The packaging can be configured in particular as a bottle or liquid container. Usually, such packaging has a lid through which the liquid, particularly in the form of a drink, can be poured out of the packaging.

Within the scope of the inspection device according to the invention, it is also conceivable that a retaining unit has a mechanical receptacle for the packaging and, if necessary, is simultaneously configured with a rotating and/or pivoting mechanism. This rotating and/or pivoting mechanism allows the package to be shaken to establish a state of equilibrium within the package and thus achieve an accurate sample measurement.

Furthermore, the inspection device according to the invention may provide that a retaining unit, in particular as a mechanical receptacle, for the packaging is configured at the same time as the rotating and/or pivoting mechanism. Thus, the packaging can be securely attached to the rotating and/or pivoting mechanism by means of the mechanical receptacle. As a result, the mechanical pickup is rotated by the rotating or pivoting mechanism, which then also moves the packaging with the food. For this purpose, a suitable drive motor may be provided on the inspection device to electromechanically drive the rotating and/or pivoting mechanism.

In the case of the inspection device according to the invention, it is further conceivable that at least one of the following sensors is present: temperature sensor, pressure sensor, optical sensor, weight sensor, humidity sensor, capacitive or inductive sensor, resistance sensor and the like, in each case in particular as part of the detection arrangement. So-called combination sensors, which can measure several properties, can also be used.

For example, a communication device of the inspection device is configured as a Bluetooth interface or as a serial interface or as a USB interface or as a barcode and/or QR code interface (e.g. as a scanner) or as an acoustic interface or as an NFC interface or as a network interface (e.g. WLAN) or as a mobile radio interface or the like, in order to enable a corresponding (in particular wireless) communication of the inspection device with a mobile communication device and/or a data processing system and/or the like, for example also via an Internet connection. This communication can be used, for example, to transmit a detecting result from the inspection device and/or to transmit an inspection result to the inspection device. The communication is e.g. uni- or bidirectional. Alternatively or in addition, an input device is provided on the inspection device for operating the inspection device (e.g. manually selecting food and/or packaging information to determine calibration information). For this purpose, the input device comprises, for example, at least one push-button and/or touch screen and/or voice interface and/or the like.

Furthermore, it may be possible for the inspection device according to the invention and/or an external device (for this purpose), such as a mobile communication device, to have a sensor element for the detection of information about the food and/or the packaging. The sensor element is configured, for example, as an image sensor or as an NFC or RFID sensor or the like to detect, for example, a type of food or packaging. For this purpose, peculiarities of the packaging (such as an imprint or a transponder) can be inspected.

Within the scope of the inspection device according to the invention, it is also possible that at least one light source (radiation source), in particular in the form of a laser, is present and that the emitted light from a light source is measurable by an optical sensor. Of course, several light sources can also be arranged geometrically to each other in the inspection device, in order to also optically measure a measuring section or a measuring field. As optical sensors, so-called line sensors or array sensors can measure the light emitted by the light source. A control of the light source as well as an inspection of the detected metrological signals from the optical sensor(s) can be performed by the inspection unit in the inspection device. At the same time, the optical measurement data obtained can be compared, processed and/or stored with measurement data from a sensor located inside the packaging. Of course, the optical measurement can also be performed separately from the direct sample measurement.

Furthermore, according to the invention, it is conceivable that the inspection device according to the invention has at least one temperature control unit for tempering the packaging with the food. The temperature control unit is used to bring the packaging with the food to a predefined temperature so that measurement errors due to different temperatures are prevented. Furthermore, it is thus possible that at least in the case of indirect, non-destructive sample measurement, the cooling of the food is not interrupted during the measurement.

Further advantages, features and details of the invention result from the following description, in which embodiments of the invention are described in detail with reference to the drawings. The features mentioned in the claims and in the description may be inventive by themselves or in any combination. It is shown:

Figure 1:
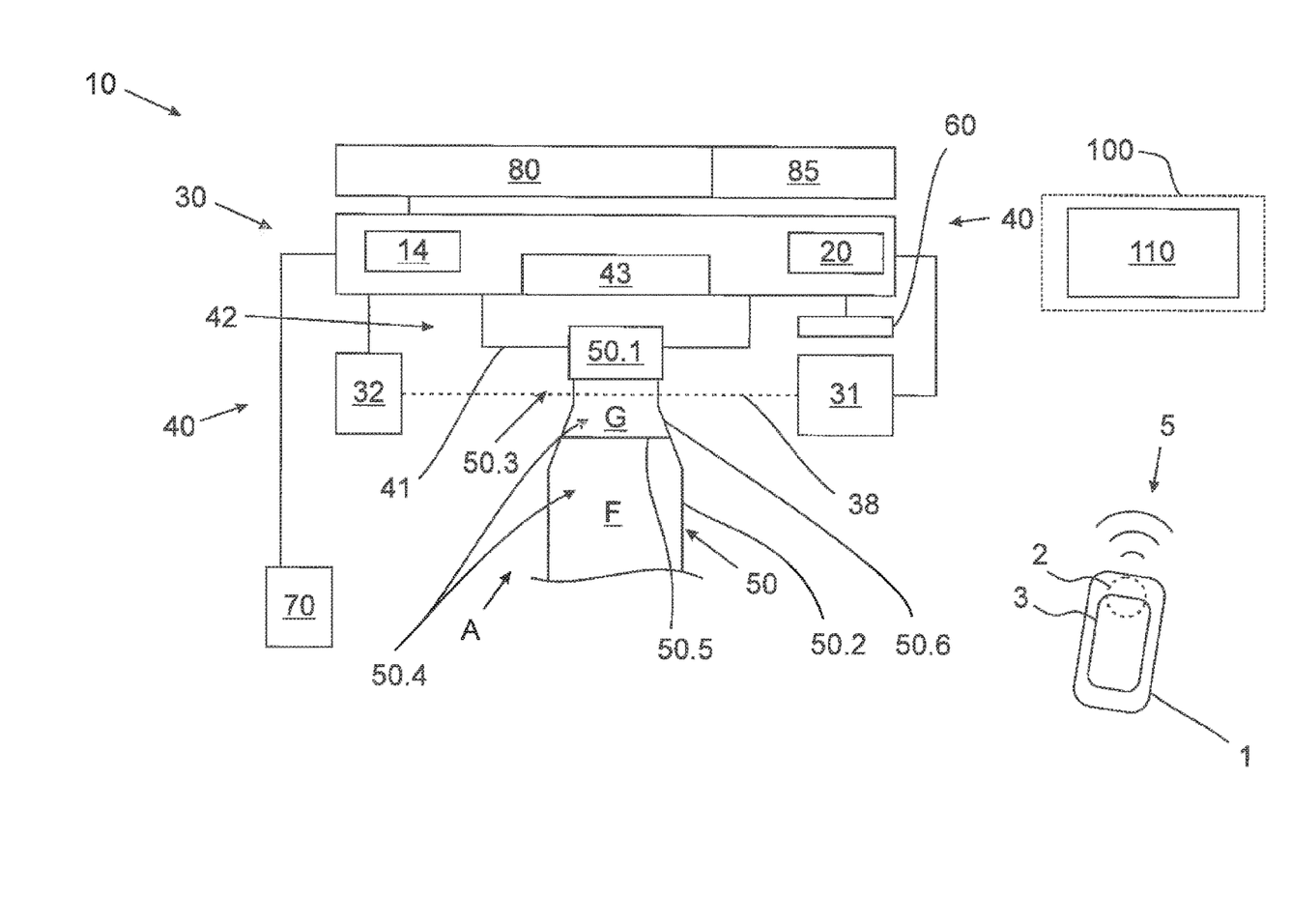
FIG. 1 a schematic diagram of a system according to the invention with an inspection device according to the invention.

FIG. 1 schematically shows an inventive system with an inventive inspection device 10. For this purpose, the system is used for inspecting food 50.4 in packages 50, preferably in bottles 50.2 For this purpose, the system may comprise the inspection device 10 and/or a mobile communication device 1, such as a smartphone or the like, and/or a data processing system 100, in particular an external server 100.

In the embodiments shown, the food 50.4 is exemplarily configured as a beverage, which is contained in a bottle 50.2 as packaging 50. Here a filling level 50.5 is also shown, whereby above the filling level 50.5 there is a gas phase G in the closed bottle 50.2 and below the filling level 50.5 there is a liquid F. For example, one wall of bottle 50.2 is at least partially transparent. A closure 50.1, in particular a lid 50.1, may be fitted in the head space 50.3 to provide an airtight seal for the bottle 50.2. In addition, a bottle neck 50.6 is shown, in which at least predominantly the gas phase G is located.

In the case of food 50.4 in packaging 50, a problem is that an inspection of at least one characteristic of food 50.4, e.g. a $CO_2$/N2 content, can only be determined extensively. Frequently, the packaging 50 must be opened, e.g. when a torque is determined for the closure 50.1 (or the lid 50.1) of packaging 50.

Therefore, according to the invention, an inspection device 10 can be used, which enables a non-destructive (especially optical) inspection. For this purpose, a positioning structure 40 is provided, to which, among other things, a detection arrangement 30, in particular detection arrangement 30 at least for pressure measurement, is mechanically connected. This has the advantage that the positioning structure 40 allows the detection arrangement 30 to be arranged and/or aligned with the packaging 50 (also at various predefined points/positions). For example, it may be necessary for the inspection device 10 to be centered at (exactly one or several predefined places/positions) of the packaging 50 in order to perform a correct inspection. For this purpose, the user can move the (mobile) inspection device 10 (ideally on a handle) with the help of the positioning structure 40 by rotating or swiveling (for packaging 50) at predefined places/positions in order to detect individual measurement results there. For example, the detection arrangement 30 has a transmitter unit 31, in particular a light source (radiation source), preferably a laser source, for emitting a measuring effect 38, in particular for emitting a laser beam 38. The positioning structure 40 may have such a geometrical formation and/or geometrical arrangement that the transmitter unit 31 is aligned with an arrangement area A (measuring range) when the inspection device 10 is attached to the packaging 50. This can be used to cause the measuring effect 38, in particular the laser beam 38, to pass through the (at least partially transparent) packaging 50 and through the food 50.4, in particular (possibly exclusively) through the gas phase G of the food 50.4. For example, the measuring effect 38 first hits a first point on the wall of packaging 50, then the gas phase G and then exits again through a second point on the wall of packaging 50. In this case, a change in the measuring effect 38 can be caused by the food 50.4, i.e. in particular by the gas phase G. This change can be identified, for example, in a spectrum of the measuring effect or the laser beam 38. Therefore, a receiver unit 32 can be used to receive the measuring effect 38, e.g. to detect the laser beam 38 by a photodiode of the receiver unit 32 as light detector 32. In particular, only an intensity of light 38 is detected. If, according to another advantage, a parameter, such as a wavelength, of the transmitter unit 31 is varied during this reception, a spectrum can be determined.

Now it may be possible that the acquired spectrum is analyzed by an inspection unit 14 and/or by an external device, such as a mobile communication device 1 and/or by a data processing system 100. In particular, the spectrum may include a peak, where a half-width of this peak is specific to a total pressure of the food 50.4 In other words, the pressure can be detected as a parameter of food 50.4 by means of the detecting of the receiving unit 32. In order to determine a characteristic of food 50.4, such as $CO_2$ content, another parameter may have to be detected.

For this purpose, the detection arrangement 30 can also have a temperature sensor 70, which is configured, for example, as an optical sensor, in particular with a laser, e.g. as a bolometer or pyrometer. This is also attached to the positioning structure 40 in such a way that, when the inspection device 10 is placed on the packaging 50, the temperature sensor 70 is aligned in the direction of the packaging 50, preferably the liquid F. Accordingly, the temperature sensor 70 can be located in a defined manner lower or below the receiving unit 32 and/or the transmitting unit 31, whereby the directional information refers advantageously to a direction of gravity acting on the liquid F. Accordingly, for the inspection of the package 50 with the food 50.4 should be positioned as far as possible in such a way that a horizontal filling level 50.5 (orthogonal to the direction of gravity) is reached.

It is also advantageous if the inspection device 10 has a retaining unit 41. The retaining unit 41 can be used for the positive attachment of the inspection device 10 to the packaging 50, e.g. to a closure 50.1 of the packaging 50. For this purpose, it is conceivable that the retaining unit 41 has a conical receptacle to accommodate the closure 50.1 and/or a bottle neck 50.6. This allows centering of the inspection device 10 on the packaging 50, especially on the bottle 50.2 with respect to the bottle neck 50.6 This is necessary to allow exact positioning of the transmitter unit 31 and/or the receiver unit 32 and/or the temperature sensor 70 at a predetermined distance and/or angle on the packaging 50.

Optionally, it is possible that the retaining unit 41 provides a rotating and/or pivoting mechanism 42. For example, the retaining unit 41 is configured as a so-called closure gripper (chuck), so that a torque measuring system 43 is provided to detect a torque when a closure 50.1 of package 50 is rotated. This has the advantage that for further inspection of the food 50.4 a torque can be measured by opening and/or closing the bottle 50.2, which also provides a conclusion on the gas content.

Furthermore, it is possible that the inspection device has an input device 85 for operation, which has, for example, a button for switching on and/or a (further) selection button for operation.

By using a temperature sensor 70 to measure the temperature of the food 50.4 and by evaluating the measured temperature and the measured pressure, it is possible to advantageously determine a characteristic of the food 50.4, preferably a $CO_2$ content of the food 50.4. Thus, the inspection device 10 can provide all the sensors needed to acquire the raw data for determining this characteristic. It may be possible that the inspection for determining the characteristic is performed by the inspection device 10 itself or alternatively by an external device 100, 1 using the raw data. In particular, calibration data may be necessary to determine the characteristic from the raw data.

For example, a communication device 20 may be provided on the inspection device 10 to transmit the raw data to an external device, such as a mobile communication device 1 and/or a data processing unit 100, such as a server. Accordingly, the inspection for determining the characteristic can then be performed by the external device. It may also be possible that the mobile communication device 1 serves as an intermediary to the data processing system 100. In this case, the raw data (i.e., e.g., an detection result of the detection of the detection arrangement 30) can first be transmitted from the communication device 20 to the mobile communication device 1 and then from the mobile communication device 1 to the data processing system 100 via a communication 5, e.g., via a network, in particular, a mobile radio network and/or an Internet.

The data processing system 100 and/or the mobile communication device 1 includes, for example, a database 110 in which calibration data is stored. These can be used to parameterize the detecting of detection arrangement 30 and/or to inspect the detecting result (i.e. the raw data) of the detecting. For example, the detecting and/or inspection must be performed in different ways for different packaging geometries and/or for different food. This is taken into account by the calibration data, which have been determined empirically or by laboratory measurements.

To select the appropriate calibration data, it may be advantageous to select them manually (e.g. by an input device 85) and/or automatically. For automated selection, image information about the food 50.4 and/or the packaging 50 can be used, for example, which is detected by the mobile communication device 1 and/or made available to the inspection device 10 and/or the data processing system 100, if necessary. For example, a sensor element 2, such as a camera of communication device 1, can take a picture of packaging 50 with food 50.4 and transmit it to inspection device 10 if necessary.

Subsequently, a result of the inspection, e.g. a result of the inspection, can be output by a display device 80 of inspection 10 and/or by a display device 3 of mobile communication device 1. For example, a direct output of the measured values, i.e. values about the level and/or type of the measured characteristic of the food 50.4, such as a level of the gas content, takes place. The output can also be simplified, e.g. according to a traffic light display (red-yellow-green) with three levels. For this purpose, multicolored light-emitting diodes can be used as display means 3 or as display device 80.

A particular advantage is that the inspection can be performed on the move. For this purpose, the inspection device 10 is configured as a handheld device. In order to make mobile operation possible, an energy storage 60 can be provided for mobile energy supply independent of the mains. This is configured as an accumulator, for example, and is accommodated in a housing of inspection 10.

The description above of the embodiments describes the present invention exclusively within the framework of examples. It goes without saying that individual features of the embodiments can be freely combined with each other, provided that it is technically reasonable, without leaving the scope of the present invention.

LIST OF REFERENCE SIGNS

1 Communication device
2 Sensor element
3 Display means
5 Communication
10 Inspection device
14 Inspection unit
20 Communication device
30 Detection arrangement
31 Transmitter unit, light source, laser source
32 Receiving unit, light detector, optical sensor
38 Laser beam, measuring effect
40 Positioning structure
41 Retaining unit, positioning unit
42 Turn and/or swivel mechanism
43 Torque measuring system
50 Packaging
50.1 Cover
50.2 Bottle, liquid container
50.3 Head space
50.4 Food, particularly beverages
50.5 Filling level
50.6 Bottle neck
60 Energy storage device, energy supply
70 Temperature sensor
80 Display device
85 Input device
100 Data processing system, server
110 Database
A Arrangement area
F Fluidity
G Gas phase

The invention claimed is:

1. An inspection device for inspection, for non-destructive pressure and temperature measurement, comprising
    a detection arrangement for detecting at least one parameter in a food in a package, wherein the parameter is a gas content of the food in the package,
    wherein,
    the inspection device is configured as a handheld device,
    the detection arrangement comprises a transmitter for transmitting a measuring effect and a receiver for detecting the transmitted measuring effect,
    the transmitter is configured as a laser source, and the receiver is configured as an optical sensor and the measuring effect is configured as laser radiation, in order to detect a change in a spectrum of the radiation which is specific for the parameter, and
    a positioning structure is provided in order to perform an external positioning of the detection arrangement on the package.

2. The inspection device according to claim 1,
    wherein,
    the at least one parameter further includes a pressure or a temperature at the food.

3. The inspection device according to claim 1,
    wherein,
    a positioning structure is provided for at least partially arranging the package with the food in an arrangement area as a measuring area, wherein the transmitter and the receiver of the detection arrangement are aligned with the measuring area by the positioning structure.

4. The inspection device according to claim 1,
    wherein,
    a communication device is provided for performing a at least wireless, data communication with a mobile communication device or a central data processing system in order to transmit a result of the detection via the data communication.

5. The inspection device according to claim 1,
    wherein, a retainer, preferably a positioner, is possible to attach the inspection device to the packaging.

6. The inspection device according to claim 1, wherein,
a retainer is possible, which is configured as a closure gripper for torque measurement in order to be attached to a bottle closure of the packaging configured as a bottle.

7. The inspection device according to claim 1, wherein,
there is the possibility that a retainer is configured for adaptation to a head space of a package configured as a bottle, preferably in order to attach the inspection device concentrically to a bottle closure.

8. The inspection device according to claim 1, wherein,
a retainer is providable and is configured as a centering unit, so that the inspection device is centered on the packaging in a measuring position by the retainer.

9. The inspection device according to claim 1, wherein,
the transmitter is aligned with the receiver and an arrangement region in such a way that a measuring effect first reaches the arrangement region and then the receiver in order to detect a change in the measuring effect caused by the food.

10. The inspection device according to claim 1, wherein,
a display device is provided for displaying a multi-stage inspection result.

11. The inspection device according to claim 1, wherein,
an energy storage device, preferably an accumulator, is provided for portable operation of the inspection device for mobile energy supply.

12. The inspection device according to claim 1, wherein,
the detection arrangement comprises an optical temperature sensor for detecting a temperature at the food in the package.

13. A system for inspecting, for non-destructive pressure and temperature measurement, comprising:
an inspection device for detecting at least one parameter in a food in a package, the parameter being specific to a characteristic of the food to be inspected, and
an inspector for evaluating the detection in order to determine the characteristic of the food to be inspected, wherein,
the inspection device is configured according to claim 1.

14. The system according to claim 13, wherein,
the inspector is part of the inspection device, so that the inspection is performed by the inspection device.

15. The system according to claim 13, wherein,
the optional use of a mobile communication device is provided which comprises the inspector in order to perform the inspection separately from the inspection device.

16. The system according to claim 13, wherein,
optionally a mobile communication device is provided which has at least one sensor element for detecting information about the food in the packaging separately from the inspecting device, so that the inspection, is performed as a function of the detected information and the detected parameter.

17. The system according to claim 13, wherein,
the inspection device is configured as an inspection device for inspection, comprising
a detection arrangement for detecting at least one parameter in a food in a package, wherein the parameter is specific for a characteristic of the food to be inspected,
wherein,
the inspection device is configured as a handheld device.

18. A method of inspection, for non-destructive pressure and temperature measurement, for measuring a gas content, of food in packages,
wherein,
the following steps are performed:
a) mobile detection of at least one parameter in a food in a package by a portable inspecting device, wherein the parameter is specific to a characteristic of the food to be inspected,
b) inspect at least the detection of at least one parameter to determine an inspection result, and
c) output of the inspection result,
wherein the portable inspecting device is configured according to claim 1.

19. The method according to claim 18, wherein,
prior to step a), information, preferably image information, is detected by an optical sensor element, preferably of a mobile communication device, about at least the packaging or the food in the packaging, and in step b) the inspection is performed using this information, preferably in order to take into account at least the type of packaging or the food.

20. The method according to claim 18, wherein,
prior to step a), at least one item of information about at least the packaging or about the food is transmitted to an external data processing system by means of a communication of the inspecting device or of a mobile communication device, and at least one item of calibration information is determined on the basis of a database of the data processing system as a function of the transmitted information, in order to perform the detection according to at least step a) or the inspection according to step b) on the basis of the calibration information.

21. The method according to claim 18, wherein,
at least step a) or b) or c) is performed autonomously by the inspection device.

22. The method according to claim 18, wherein,
at least steps b) or c) are performed at least partially by an external device, preferably by at least the data processing system or by the mobile communication device, with data communication of the inspection device preferably taking place for this purpose via a data network with the external device.

23. The method according to claim 18, wherein,
the detection according to at least step a) or the inspection according to step b) comprises a spectroscopic inspection of electromagnetic waves.

24. The method according to claim 18, wherein,
prior to step b), at least one geometric characteristic of the packaging is recorded by measurement, preferably by a mobile communication device, preferably by image detection, and is inspected at step b).

25. The method according to claim 18, wherein, according to at least step a) at least the temperature or the pressure is measured in order to determine a gas content in the package from the measured values of this measurement, preferably as a function of at least one calibration information which is determined as a function of the food in the package.

26. The method according to claim 18, wherein, an inspecting device is operated as an inspection device for inspection, comprising     a detection arrangement for detecting at least one parameter in a food in a package, wherein the parameter is specific for a characteristic of the food to be inspected, wherein, the inspection device is configured as a handheld device or a system as an inspection device for inspection, comprising     a detection arrangement for detecting at least one parameter in a food in a package, wherein the parameter is specific for a characteristic of the food to be inspected, wherein, the inspection device is configured as a handheld device.

\* \* \* \* \*